United States Patent
Molla et al.

(10) Patent No.: US 12,392,241 B2
(45) Date of Patent: Aug. 19, 2025

(54) DETERMINING RESERVOIR FLUID PROPERTIES FROM DOWNHOLE FLUID ANALYSIS DATA USING MACHINE LEARNING

(71) Applicant: Schlumberger Technology Corporation, Sugar Land, TX (US)

(72) Inventors: Shahnawaz Molla, Watertown, MA (US); Farshid Mostowfi, Lexington, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 531 days.

(21) Appl. No.: 17/416,773

(22) PCT Filed: Dec. 18, 2019

(86) PCT No.: PCT/US2019/067060
§ 371 (c)(1),
(2) Date: Jun. 21, 2021

(87) PCT Pub. No.: WO2020/131996
PCT Pub. Date: Jun. 25, 2020

(65) Prior Publication Data
US 2022/0074303 A1      Mar. 10, 2022

Related U.S. Application Data

(60) Provisional application No. 62/783,842, filed on Dec. 21, 2018.

(51) Int. Cl.
E21B 49/08        (2006.01)
E21B 47/07        (2012.01)
(Continued)

(52) U.S. Cl.
CPC .............. *E21B 49/08* (2013.01); *E21B 47/07* (2020.05); *E21B 49/0875* (2020.05);
(Continued)

(58) Field of Classification Search
CPC ...... E21B 49/08; E21B 47/07; E21B 49/0875; E21B 2200/22; E21B 49/10; E21B 41/00;
(Continued)

(56) References Cited

U.S. PATENT DOCUMENTS 6,476,384 B1    11/2002    Mullins et al.
6,956,204 B2    10/2005    Dong et al.
(Continued)

FOREIGN PATENT DOCUMENTS

WO    2006063094 A1    6/2006

OTHER PUBLICATIONS

Substantive Exam issued in Saudi Arabia Patent Application No. 521422347 dated Jun. 13, 2023, 13 pages.
(Continued)

*Primary Examiner* — Alexander Satanovsky
(74) *Attorney, Agent, or Firm* — Jeffrey D. Frantz

(57) ABSTRACT

Methods for determining in situ the value of a formation fluid parameter using a downhole fluid analysis (DFA) tool. The methods utilize advanced statistical learning tools to build a predictive model to estimate a fluid property given a set of input parameters. In one embodiment the fluid saturation pressure parameter is determined by using the DFA tool to obtain the fluid and to obtain weight fractions of at least $C_1$, $C_{6+}$, and $CO_2$ of the fluid. The weight fractions and a reservoir temperature are input into a trained statistical learning machine to obtain a determination of the saturation pressure of the fluid.

17 Claims, 8 Drawing Sheets

(51) Int. Cl.
*G01N 21/31* (2006.01)
*G01N 21/59* (2006.01)
*G01N 33/28* (2006.01)
*G06N 20/00* (2019.01)

(52) U.S. Cl.
CPC ......... *G01N 21/31* (2013.01); *G01N 33/2823* (2013.01); *G06N 20/00* (2019.01); *G01N 2021/5919* (2013.01)

(58) Field of Classification Search
CPC .... E21B 47/06; G01N 21/31; G01N 33/2823; G01N 2021/5919; G06N 20/00; G01J 3/18; G01J 3/36; G01J 3/02; G01J 3/00; G01V 8/10
See application file for complete search history.

(56) References Cited

U.S. PATENT DOCUMENTS

| | | | |
|---|---|---|---|
| 7,305,306 | B2 | 12/2007 | Venkataramanan et al. |
| 7,458,258 | B2 | 12/2008 | Xian et al. |
| 7,526,953 | B2 | 5/2009 | Goodwin et al. |
| 7,586,087 | B2 | 9/2009 | Dong et al. |
| 7,822,554 | B2 | 10/2010 | Zuo et al. |
| 7,920,970 | B2 | 4/2011 | Zuo et al. |
| 7,966,273 | B2 | 6/2011 | Hegeman et al. |
| 7,996,154 | B2 | 8/2011 | Zuo et al. |
| 8,434,356 | B2 | 5/2013 | Hsu et al. |
| 8,619,256 | B1 * | 12/2013 | Pelletier .............. C04B 40/0032 356/336 |
| 8,805,617 | B2 | 8/2014 | Zuo et al. |
| 8,825,408 | B2 | 9/2014 | Freed et al. |
| 9,109,434 | B2 | 8/2015 | Indo et al. |
| 9,442,217 | B2 | 9/2016 | Pomerantz et al. |
| 10,228,325 | B2 | 3/2019 | Zuo et al. |
| 2009/0030858 | A1 * | 1/2009 | Hegeman .................. G06N 3/02 166/264 |
| 2009/0182693 | A1 | 7/2009 | Fulton et al. |
| 2012/0316787 | A1 * | 12/2012 | Moran .................... E21B 44/00 702/9 |
| 2013/0327522 | A1 | 12/2013 | Glasbergen et al. |
| 2016/0063402 | A1 * | 3/2016 | Webb .................. G06Q 10/067 705/348 |
| 2017/0284199 | A1 * | 10/2017 | Indo ........................ E21B 49/10 |
| 2017/0328202 | A1 * | 11/2017 | Hsu ........................ E21B 49/10 |
| 2018/0010429 | A1 * | 1/2018 | Willberg ................. E21B 43/26 |

OTHER PUBLICATIONS

Dong, C., et al., New Downhole-Fluid-Analysis Tool for Improved Reservoir Characterization. SPE Reservoir Evaluation & Engineering, 2008. 11(6): p. 1107-1116.
Lázaro, M., et al., Support Vector Regression for the simultaneous learning of a multivariate function and its derivatives. Neurocomputing, 2005. 69(1): p. 42-61.
International Search Report and Written Opinion issued in the PCT Application PCT/US2019/067060, dated Apr. 16, 2020 (12 pages).
Examination Report issued in United Kingdom Patent Application No. GB2108708.5 dated May 26, 2022, 3 pages.
James, G., et al., An Introduction to Statistical Learning with Applications in R. Springer Texts in Statistics. 2013, (pp. 15-29).
Hastie, T., R. Tibshirani, and J. Friedman, The Elements of Statistical Learning. Springer Series in Statistics. 2009 (pp. 415-439).
International Preliminary Report on Patentability issued in the PCT Application PCT/US2019/067060, dated Jul. 1, 2021(9 pages).
2nd Substantive Exam issued in Saudi Arabia Patent Application No. 521422347 dated Jan. 18, 2024, 14 pages.

* cited by examiner

DETERMINING RESERVOIR FLUID PROPERTIES FROM DOWNHOLE FLUID ANALYSIS DATA USING MACHINE LEARNING

CROSS-REFERENCE TO RELATED APPLICATION(S)

The application is a National Stage Entry of International Application No. PCT/US2019/067060, filed Dec. 18, 2019, which claims priority from U.S. Ser. No. 62/783,842, filed Dec. 21, 2018, the complete disclosure of which is hereby incorporated by reference herein.

FIELD

The subject disclosure generally relates to methods and systems for assessing hydrocarbon reservoirs and for performing wellsite operations. More particularly, the subject disclosure relates to methods for assessing reservoir fluid properties in situ such as the saturation pressure of a reservoir fluid by utilizing machine learning techniques, although the disclosure is not limited thereto and may be used to assess other fluid properties.

BACKGROUND

In the development of oil and gas fields, it is common for oil and gas companies to explore formations in order to find, assess, produce, and sell fluid hydrocarbons. Throughout the process, the oil and gas companies desire information associated with the value of the reservoir fluids and a quantification of the uncertainty associated therewith.

One manner of obtaining and providing useful information regarding the hydrocarbons in an earth formation is to drill one or more boreholes and to run borehole tools into the formation. The InSitu Fluid Analyzer (a trademark of Schlumberger) is a downhole tool that extracts test samples of hydrocarbons from a formation and conducts a real-time downhole fluid analysis (DFA) through the use of optical absorption spectroscopy. More particularly, the InSitu Fluid Analyzer may use a grating spectrometer in addition to a conventional filter array spectrometer. The filter array spectrometer measures wavelengths in the visible (VIS) to near-infrared (NIR) range from 400 to 2100 nm across twenty channels that indicate the color and molecular vibration absorptions of the reservoir fluid and also show the main absorption peaks of water and carbon dioxide. The grating spectrometer has sixteen channels focused on the 1600 to 1800 nm range where reservoir fluid has characteristic absorptions that reflect molecular structure. The fluid analysis may include determinations of fluid hydrocarbon composition (C1, C2, C3-C5, $C_{6+}$), gas/oil ratio (GOR), live-oil density, carbon dioxide (CO2) content, fluid color, free-gas, reservoir water resistivity and pH, oil-base mud filtrate contamination, etc. See, e.g., co-owned U.S. Pat. Nos. 6,476,384, 6,956,204, 8,805,617, 7,458,258, 7,526,953, 7,305,306, all of which are hereby incorporated by reference herein in their entireties. Other borehole tools may be run in conjunction with the InSitu Fluid Analyzer, including, by way of example only, sonic tools, neutron tools, and gamma-ray tools which may provide additional information about the formation geology and fluid content. The InSitu Fluid Analyzer tool and/or one or more other tools may include temperature and pressure sensors.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

It is desirable to know the fluid saturation pressure of downhole fluids in a formation being analyzed. The fluid saturation pressure is the pressure of the fluid when the vapor is in equilibrium with its liquid; i.e., the pressure at which the gas and liquid phases do not separate. The fluid saturation pressure is a particularly important factor in the sampling of formation fluids by a downhole fluid analyzer because the speed at which formation fluids may be collected is related to the pressure differential between the downhole fluid analyzer tool and the formation. If, in order to quickly conduct fluid sampling, the pressure of the DFA tool is dropped below the fluid saturation pressure of the formation fluids, the fluid sample obtained may not be representative of the fluid in the formation; e.g., a higher percentage of gas than is representative of the fluid as a whole may be obtained. On the other hand, if the pressure of the DFA tool is kept very close to the formation pressure, significant amounts of time may be required to collect a representative fluid sample, thereby significantly increasing the expense of the procedure. Accordingly, in one aspect, it is desirable to know the fluid saturation pressure so as to set the sampling pressure slightly above the fluid saturation pressure in order to obtain a good sample as quickly as possible.

As previously suggested, downhole fluid analyzer tools use downhole spectrometry to collect optical information of fluid flowing in a flow line of the tool, and the optical information is used to make determinations of fluid hydrocarbon composition, gas/oil ratio (GOR), live-oil density, carbon dioxide content, fluid color, free-gas, reservoir water resistivity and pH, oil-base mud filtrate contamination, etc. However, neither DFA tools nor other borehole tools have been able to provide information regarding the fluid saturation pressure of the formation fluid while the tool is functioning downhole (in situ).

In one aspect, methods are provided herein to determine in situ the fluid saturation pressure of formation fluid using a DFA tool. The methods utilize advanced statistical learning tools to build a predictive model to estimate fluid properties given a set of input parameters from a DFA tool. More particularly, in one embodiment, a dataset of fluid properties for fluid samples including reservoir pressure ($P_{res}$) and reservoir temperature ($T_{res}$) for the sample, as well as lab-obtained fluid composition ($C_1$, $C_2$, $C_3$-$C_5$, $C_{6+}$, $CO_2$ wt %) and saturation pressure ($P_{sat}$) are collected for multiple samples. The dataset or a subset thereof are then used as input parameters for a statistical model. Feature selection may be guided by correlations between $P_{sat}$ and other parameters. The dataset may be randomly split into a training set subset and a testing set subset. The training set may then be used to train an SVM (support vector machine) regression model which estimates the saturation pressure of samples based on the input parameters. Once the regression model is trained, a DFA tool may be located downhole, actuated to collect a sample, and the parameters, as determined by the DFA tools may be input into the trained regression model in order to determine in situ the formation fluid saturation pressure. The determined $P_{sat}$ may then be used to adjust the drawdown pressure of the tool.

Further features and advantages of the subject disclosure will become more readily apparent from the following detailed description when taken in conjunction with the accompanying drawings.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein.

DETAILED DESCRIPTION

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

Figure 1:
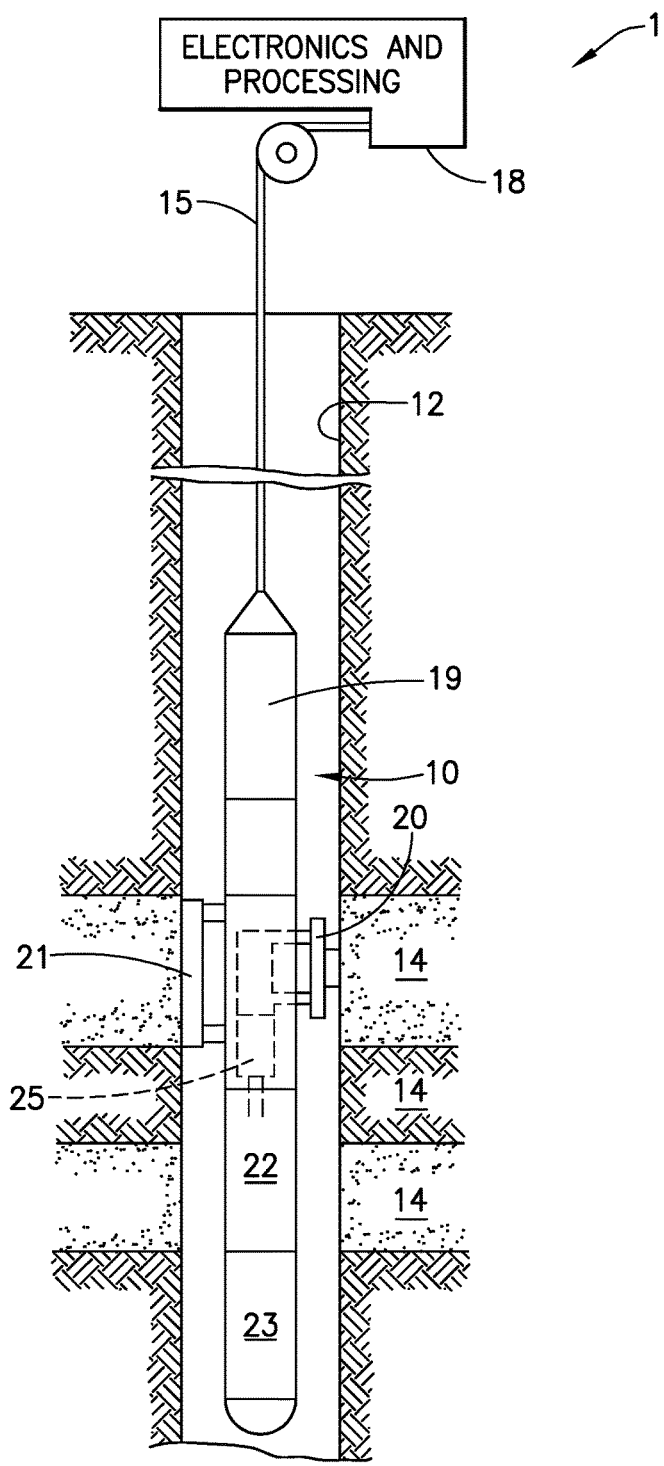
FIG. 1 is a schematic diagram of a tool string having a downhole fluid analysis (DFA) module.

Turning to FIG. 1, a petroleum reservoir analysis system 1 is shown. The system 1 includes a borehole tool 10 suspended in the borehole 12 from the lower end of a typical multiconductor cable 15 that is spooled in a usual fashion on a suitable winch on the formation surface. The cable 15 is electrically coupled to an electrical control system 18 on the formation surface. The borehole tool 10 includes an elongated body 19 which carries a selectively extendable fluid admitting assembly 20 and a selectively extendable tool anchoring member 21 which are respectively arranged on opposite sides of the tool body. The fluid admitting assembly 20 is equipped for selectively sealing off or isolating selected portions of the wall of the borehole 12 such that fluid communication with the adjacent earth formation 14 is established. The fluid admitting assembly 20 and borehole tool 10 include a flowline leading to a fluid analysis module 25. The formation fluid obtained by the fluid admitting assembly 20 flows through the flowline and through the fluid analysis module 25. The fluid may thereafter be expelled through a port or it may be sent to one or more fluid collecting chambers 22 and 23 which may receive and retain the fluids obtained from the formation. With the fluid admitting assembly 20 sealingly engaging the formation 14, a short rapid pressure drop can be used to break the mudcake seal. Normally, the first fluid drawn into the downhole tool 10 will be highly contaminated with mud filtrate. As the tool continues to draw fluid from the formation 14, the area near the fluid admitting assembly 20 cleans up and reservoir fluid becomes the dominant constituent. The time required for cleanup depends upon many parameters, including formation permeability, fluid viscosity, the pressure differences between the borehole and the formation, and overbalanced pressure difference and its duration during drilling. Increasing the pump rate can shorten the cleanup time, but the rate must be controlled carefully to preserve formation pressure conditions.

Figure 2:
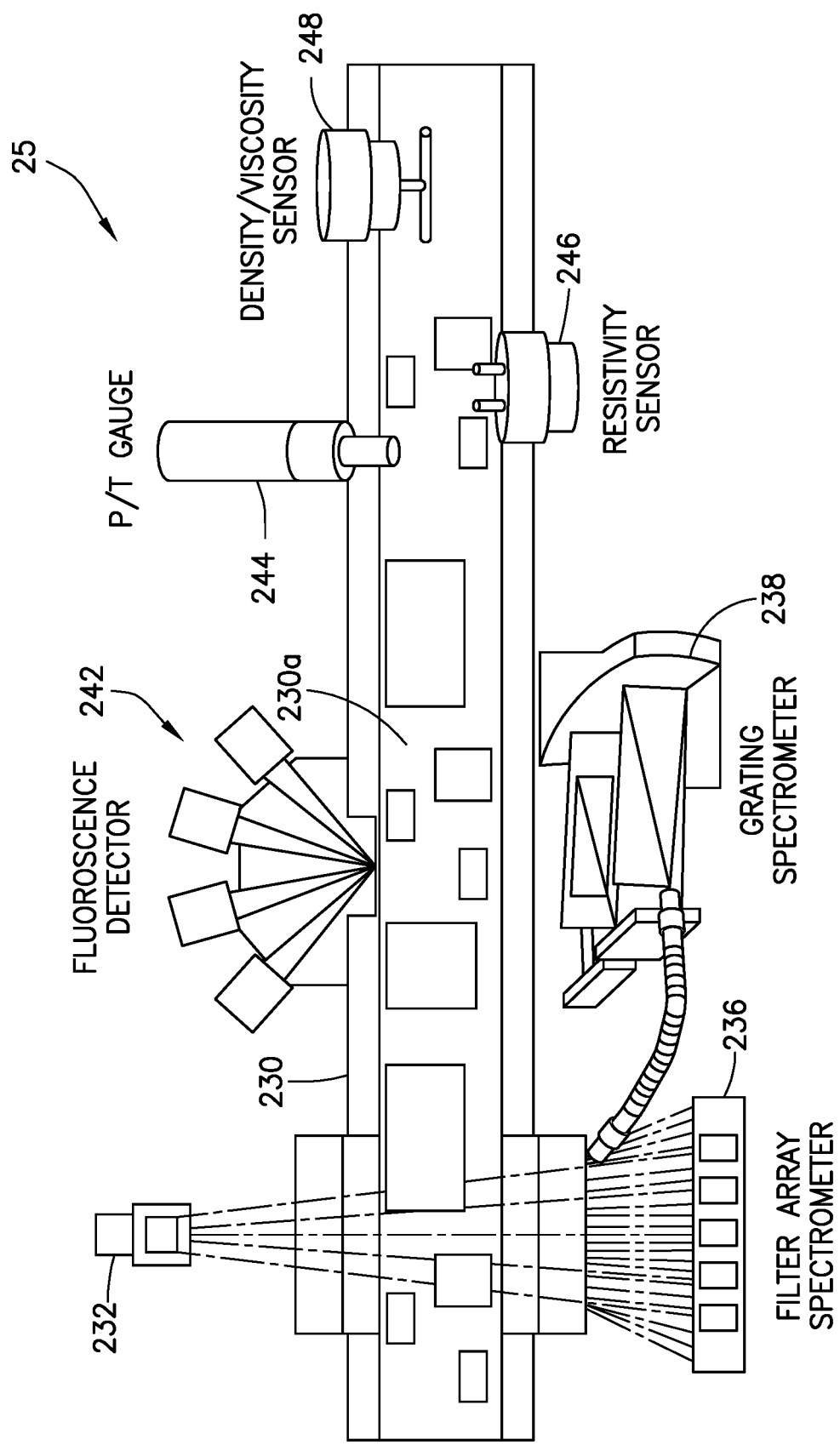
FIG. 2 is a schematic diagram of the DFA module of FIG. 1.

The fluid analysis module 25 includes means for measuring the temperature and pressure of the fluid in the flowline as described in more detail with respect to FIG. 2. The fluid analysis module 25 derives properties that characterize the formation fluid sample at the flowline pressure and temperature. In one embodiment, the fluid analysis module 25 measures absorption spectra and translates such measurements into concentrations of several alkane components and groups in the fluid sample. In an illustrative embodiment, the fluid analysis module 25 provides measurements of the concentrations (e.g., weight percentages) of carbon dioxide ($CO_2$), methane ($CH_4$), ethane ($C_2H_6$), the $C_3$-$C_5$ alkane group, the lump of hexane and heavier alkane components ($C_{6+}$), and asphaltene content. The $C_3$-$C_5$ alkane group includes propane, butane, and pentane. The $C_{6+}$ alkane group includes hexane ($C_6H_{14}$), heptane ($C_7H_{16}$), octane ($C_8H_{18}$), nonane ($C_9H_{20}$), decane ($C_{10}H_{22}$), hendecane ($C_{11}H_{24}$)—also referred to as endecane or undecane, dodecane ($C_{12}H_{26}$), tridecane ($C_{13}H_{28}$), tetradecane ($C_{14}H_{30}$), pentadecane ($C_{15}H_{32}$), hexadecane ($C_{16}H_{34}$), etc. The fluid analysis module 25 also provides a means that measures live fluid density ($\rho$) at the flowline temperature and pressure, live fluid viscosity ($\mu$) at flowline temperature and pressure (in cp), formation pressure, and formation temperature.

Control of the fluid admitting assembly 20 and fluid analysis module 25, and the flow path to the collecting chambers 22, 23 is maintained by the control system 18. As will be appreciated by those skilled in the art, the fluid analysis module 25 and the surface-located electrical control system 18 include data processing functionality (e.g., one or more microprocessors, associated memory, and other hardware and/or software) to implement the invention as described herein. The electrical control system 18 can also be realized by a distributed data processing system wherein data measured by the downhole tool 10 is communicated (preferably in real-time) over a communication link (typically a satellite link) to a remote location for data analysis as described herein. The data analysis can be carried out on a workstation or other suitable data processing system (such as a computer cluster or computing grid).

Formation fluids sampled by the downhole tool 10 may be contaminated with mud filtrate. That is, the formation fluids may be contaminated with the filtrate of a drilling fluid that seeps into the formation 14 during the drilling process. Thus, when fluids are withdrawn from the formation 14 by the fluid admitting assembly 20, they may include mud filtrate. In some examples, formation fluids are withdrawn from the formation 14 and pumped into the borehole or into a large waste chamber in the downhole tool 10 until the fluid being withdrawn becomes sufficiently clean. A clean sample is one where the concentration of mud filtrate in the sample fluid is acceptably low so that the fluid substantially represents native (i.e., naturally occurring) formation fluids. In the illustrated example, the downhole tool 10 is provided with fluid collecting chambers 22 and 23 to store collected fluid samples.

The system of FIG. 1 is adapted to make in-situ determinations regarding hydrocarbon-bearing geological formations by downhole sampling of reservoir fluid at one or more measurement stations within the borehole 12, conducting downhole fluid analysis of one or more reservoir fluid samples for each measurement station (including spectral and/or compositional analysis such as estimating concentrations of a plurality of compositional components of a given sample as well as other fluid properties), and applying the data from the fluid analysis to a trained learning module (e.g., support vector machine) which has been trained on spectral and/or compositional data in order to characterize the reservoir fluid at different locations within the reservoir as is described hereinafter. The characterization of the reservoir fluid may then be used to adjust the drawdown or flowline pressure of the tool.

Details of one embodiment of a downhole fluid analysis module 25 (such as the InSitu Fluid Analyzer of Schlumberger) is seen in FIG. 2 where module 25 shows a flow line 230 with fluid 230a therein, a light source 232 providing light in the visible and near infrared spectrum (e.g., 400 to 2100 nm), a filter array spectrometer 236 that receives light passed through the fluid flowline and measures optical absorbance of the fluid across multiple (e.g., twenty) wavelength channels in the VIS-NIR spectrum, a grating spectrometer 238 that also receives light passed through the fluid flowline and measures optical absorbance over a narrower wavelength range (e.g., sixteen channels in the 1600 to 1800 nm range), a fluorescence detector 242, a pressure and temperature gauge 244, and resistivity and density/viscosity sensors 246, 248. Absorbance data from one or both of the spectrometers may be used to identify the fluid type and quantify the weight fraction of $CO_2$ and methane, ethane, propane, n-butane, n-pentane (or $C_3$-$C_5$) and hexane plus ($C_{6+}$). Other determinations regarding the formation may likewise be made. See, e.g., co-owned U.S. Pat. Nos. 8,825,408; 7,920,970; 7,822,554; 8,434,356; 7,996,154; 9,10,434; and 10,228,325 which are hereby incorporated by reference herein in their entireties. See, also, co-owned PCT/IB2011/051230 entitled "Methods for Characterization of Petroleum Reservoirs Employing Property Gradient Analysis of Reservoir Fluids; and Dong, C. et al., *New Downhole-Fluid-Analysis Tool for Improved Reservoir Characterization*. SPE Reservoir Evaluation & Engineering, 2008. 11(6): p. 1107-1116 (2008).

According to one embodiment, the data obtained by the downhole fluid analysis module may be used to determine the saturation pressure $P_{sat}$ of the formation fluid as well as other formation fluid properties such as gas-oil ratio, molecular weight of hexane-plus fraction, etc. According to one aspect, such a determination or determinations may be made using advanced statistical learning tools which builds one or more predictive models to estimate one or more fluid properties with one or more given sets of parameters. Statistical learning refers to a wide range of tools for exploring and understanding data through statistical models.

A database containing fluid properties of fluids previously obtained from reservoirs was used to build, train and test a statistical model. Exploratory data analysis techniques were used to identify the set of input parameters that are relevant for the model. Input parameters were selected based on their respective influence on the output of the model. These statistical tools provide a means to connect the distinct measurements from the DFA sensor module to the different physical properties of the reservoir fluid.

For purposes of example, a method of estimating saturation pressure based on measurements obtained from the DFA tool 10 is hereinafter described.

A dataset was collected of fluid properties containing data such as reservoir pressure ($P_{res}$) and temperature ($T_{res}$), composition ($C_1$, $C_2$, $C_3$, $C_4$, $C_5$, $C_{6+}$, $CO_2$ wt %), saturation pressure ($P_{sat}$) etc, although only a subset of these parameters was used for determining saturation pressure. For each sample, the abovementioned fluid properties were collected from various sources, such as downhole measurements (e.g., for reservoir pressure ($P_{res}$) and temperature ($T_{res}$)), and conventional PVT laboratory measurements (for composition and saturation pressure ($P_{sat}$)—which were obtained at the reservoir pressure and temperatures at which the sample was obtained).

In this example, a workflow was developed to estimate saturation pressure of a fluid sample. It was found that the only input parameters to a statistical model required for such an estimation were $T_{res}$, $C_1$, $C_{6+}$, and $CO_2$ wt %. This feature selection was guided by the correlations between $P_{sat}$ and other parameters.

Figure 3A:
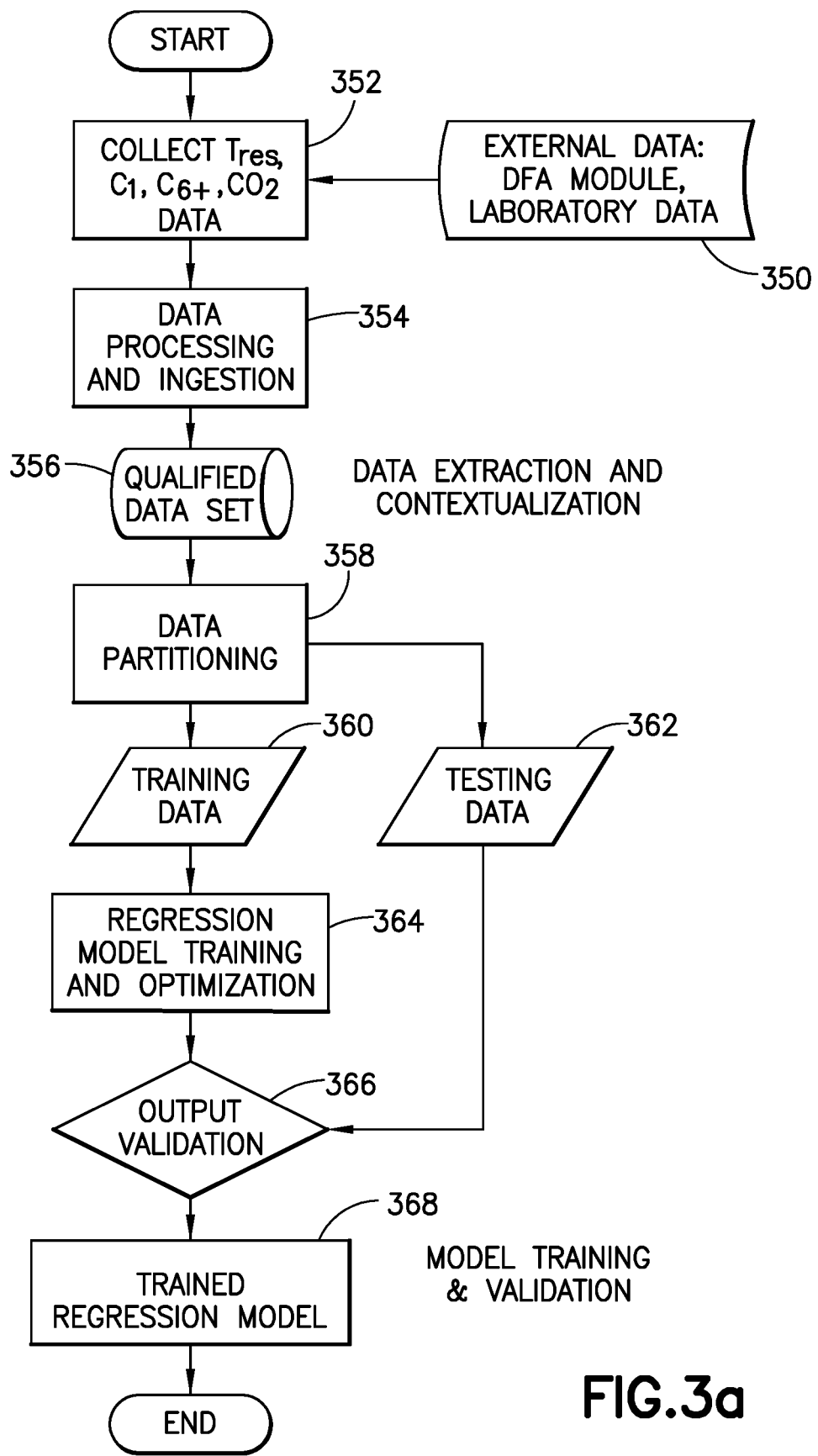
FIGS. 3a and 3b are block diagrams respectively showing workflows for training a machine learning model and for estimating fluid properties in situ from data obtained from a downhole tool using a trained machine learning model.
Figure 3B:
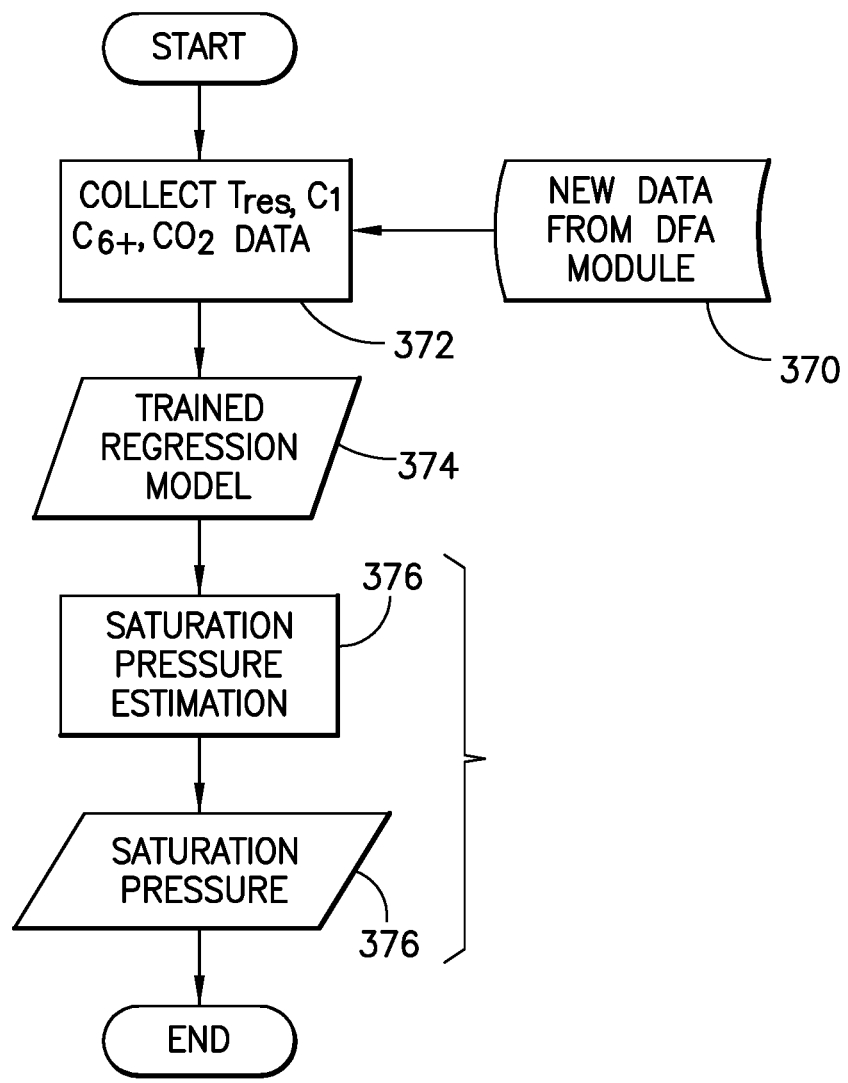
Figure 4A:
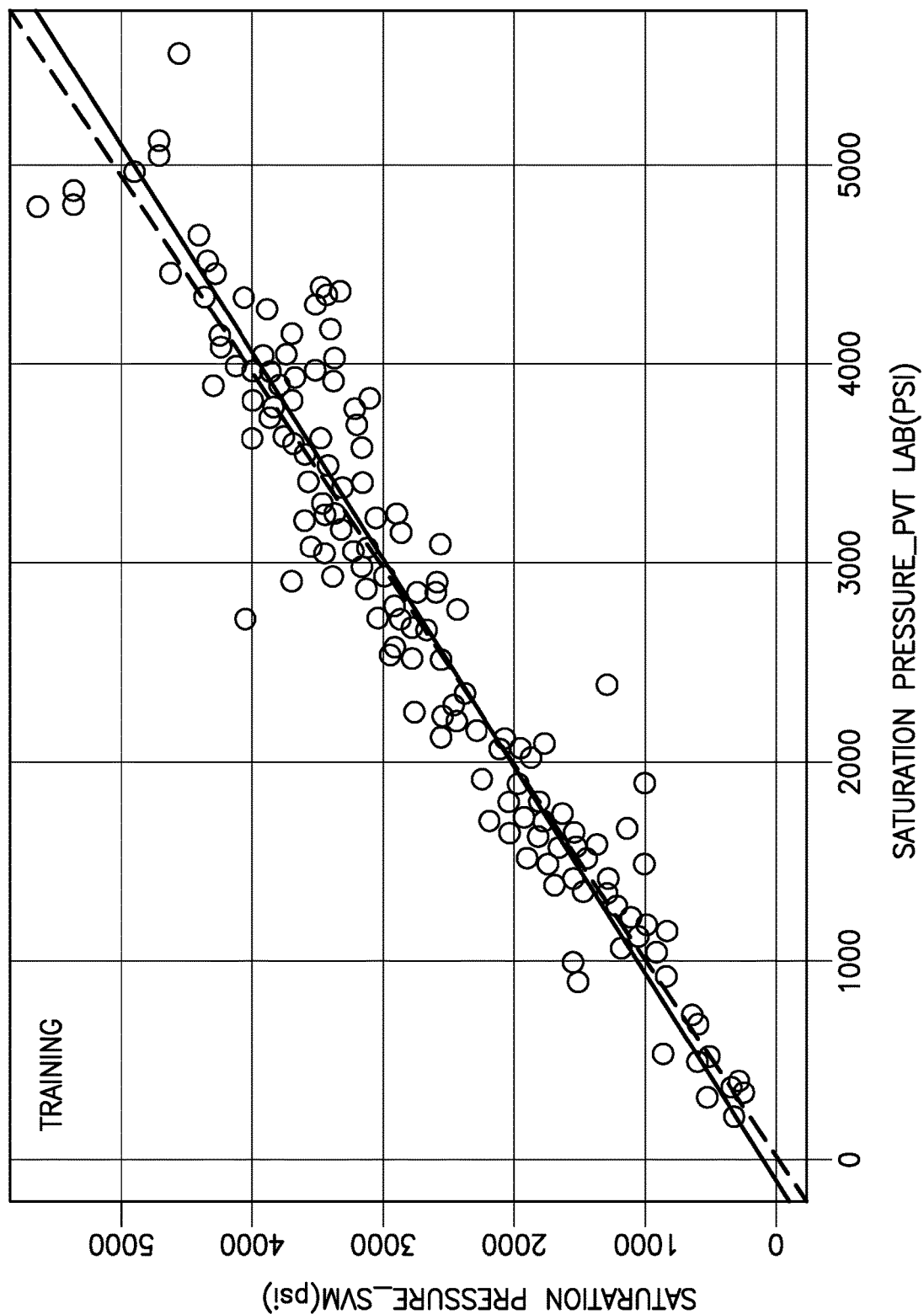
FIG. 4a is a plot showing predicted saturation pressure versus laboratory measured values for a training data set.
Figure 4B:
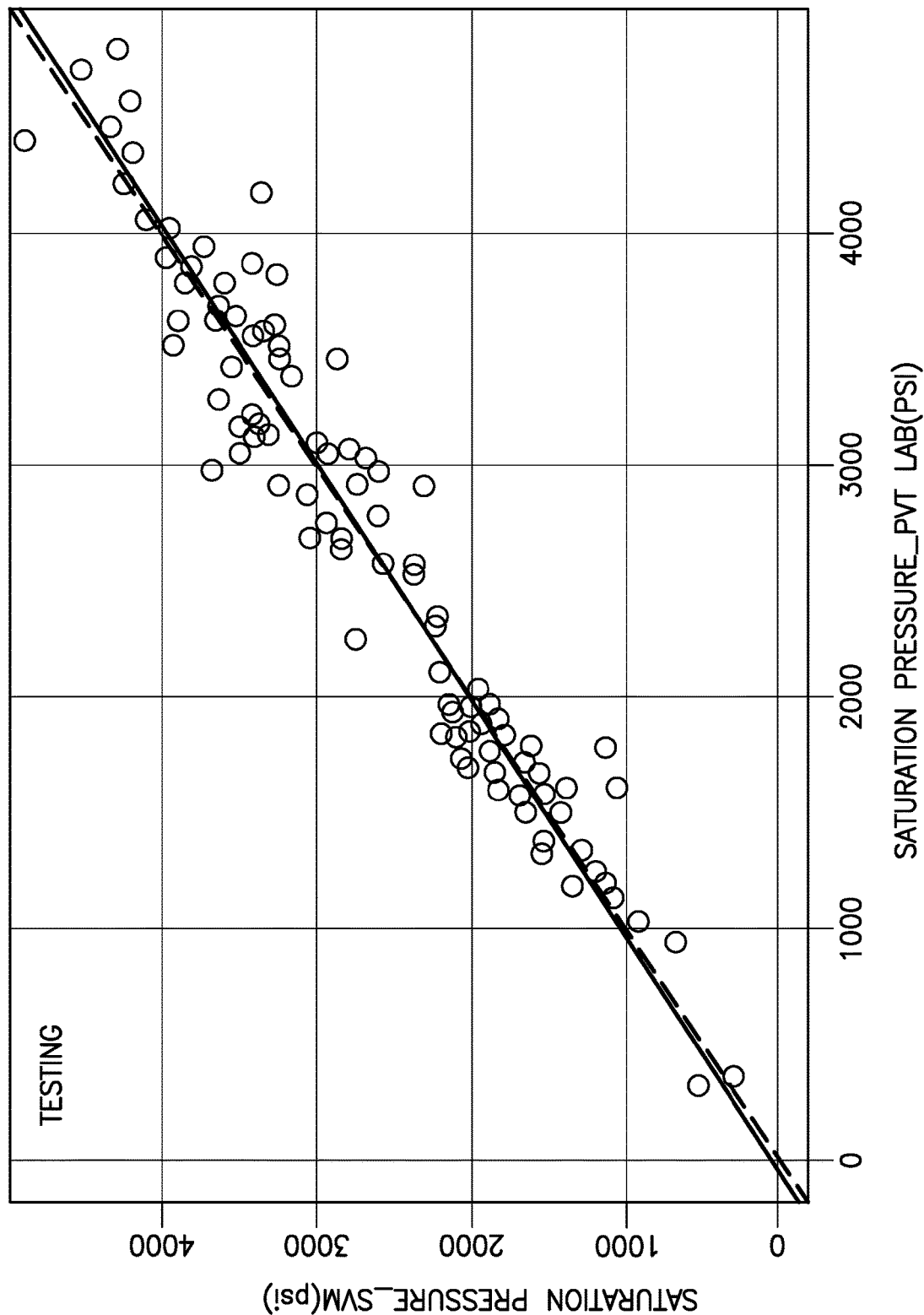
FIG. 4b is a plot showing predicted saturation pressure versus laboratory measured values for a test data set.

Details regarding the building and training of a trained machine learning model and the subsequent use of that model are seen in FIGS. 3a and 3b. See, also, James, G., et al., *An Introduction to Statistical Learning with Applications in R*. Springer Texts in Statistics, Springer-Verlag New York (2013). In particular, at 350, external data from three hundred eighty samples were obtained. The external data included data from DFA modules and from a PVT laboratory and provided ($P_{res}$) and temperature ($T_{res}$), composition ($C_1$, $C_2$, $C_3$, $C_4$, $C_5$, $C_{6+}$, $CO_2$ wt %) and the saturation pressure ($P_{sat}$) for each sample. From that data, the $C_1$, the $C_{6+}$, the $CO_2$ and the $T_{res}$ were culled 352 and provided to an SVM regression model at 354 for data processing and ingestion. At 356, outliers were removed from the dataset based on a consistency check to generate a qualified dataset. Then, at 358, the dataset was randomly split into two parts: 75% of the dataset (i.e., the training set 360) was reserved for training; and the remaining 25% of the dataset (i.e., test set 362) was used for testing the model. At 364, the regression model was trained and optimized to estimate the saturation pressure ($P_{sat}$) of samples based on the input parameters ($T_{res}$, $C_1$, $C_{6+}$, $CO_2$). The SVM regression model used a radial kernel (radial basis function) and was optimized using 10-fold cross-validation. See, Lázaro, M., et al., *Support Vector Regression for the simultaneous learning of a multivariate function and its derivatives*. Neurocomputing, 2005, 69(1): p. 42-61 (2005), and Hastie, T., R. Tibshirani, and J. Friedman, *The Elements of Statistical Learning*. Springer Series in Statistics; Springer-Verlag New York. 745 (2009). The radial kernel was selected due to its superior performance over other kernels. The radial kernel parameters (gamma and cost) were optimized for best performance. The learning performance of the trained model is shown in FIG. 4a. The parity plot of FIG. 4a shows comparison between the predicted saturation pressure using the regression model versus the laboratory measured saturation pressure of the samples in the training set. The model predictions for the training set agreed reasonably well with the laboratory measurements, except for a few cases. The absolute error ($|P_{sat,Lab} - P_{sat,SVM}|$) of the predicted values were less than 200 psi for 67% of the samples and less than 500 psi for 91% of the samples. The model was then used at 366 to predict the saturation pressure of the test set data 362; i.e., output validation. Results are shown on a parity plot in FIG. 4b. The absolute error ($|P_{sat,Lab} - P_{sat,SVM}|$) in the predicted values were less than 200 psi for 66% of the samples and less than 500 psi for 89% of the samples. The prediction on the test set was in agreement with the model performance for the training set, thereby confirming at 368 that the regression model was properly trained.

Once the machine learning model (e.g., the SVM regression model) has been trained, a determination of saturation pressure may be made by running one or more borehole tools to collect at least the necessary information for the model and applying data to the model and running the model to provide a determination. Thus, as seen in FIG. 3*b*, a DFA borehole tool is run at 370 to collect information regarding the reservoir temperature as well as specific formation fluid data including at least weight percentages of carbon dioxide, methane, and $C_{6+}$ in the formation fluid at 372. The information is provided at 374 to the trained machine learning (e.g., SVM regression) model which is typically embodied in a processor on the DFA borehole tool 10 or uphole, and the model is run to provide an estimation or determination of saturation pressure at 376.

According to one aspect, while an SVM algorithm or model was described as being used for machine learning, it will be appreciated that other statistical learning algorithms can be implemented in this workflow. The statistical model selection is guided by the features present in the training data as well as the desired output of the model. Thus, while a supervised learning approach was described, unsupervised learning algorithms could be utilized. Similar workflow can be developed to estimate other fluid properties from DFA measurements.

Figure 5:
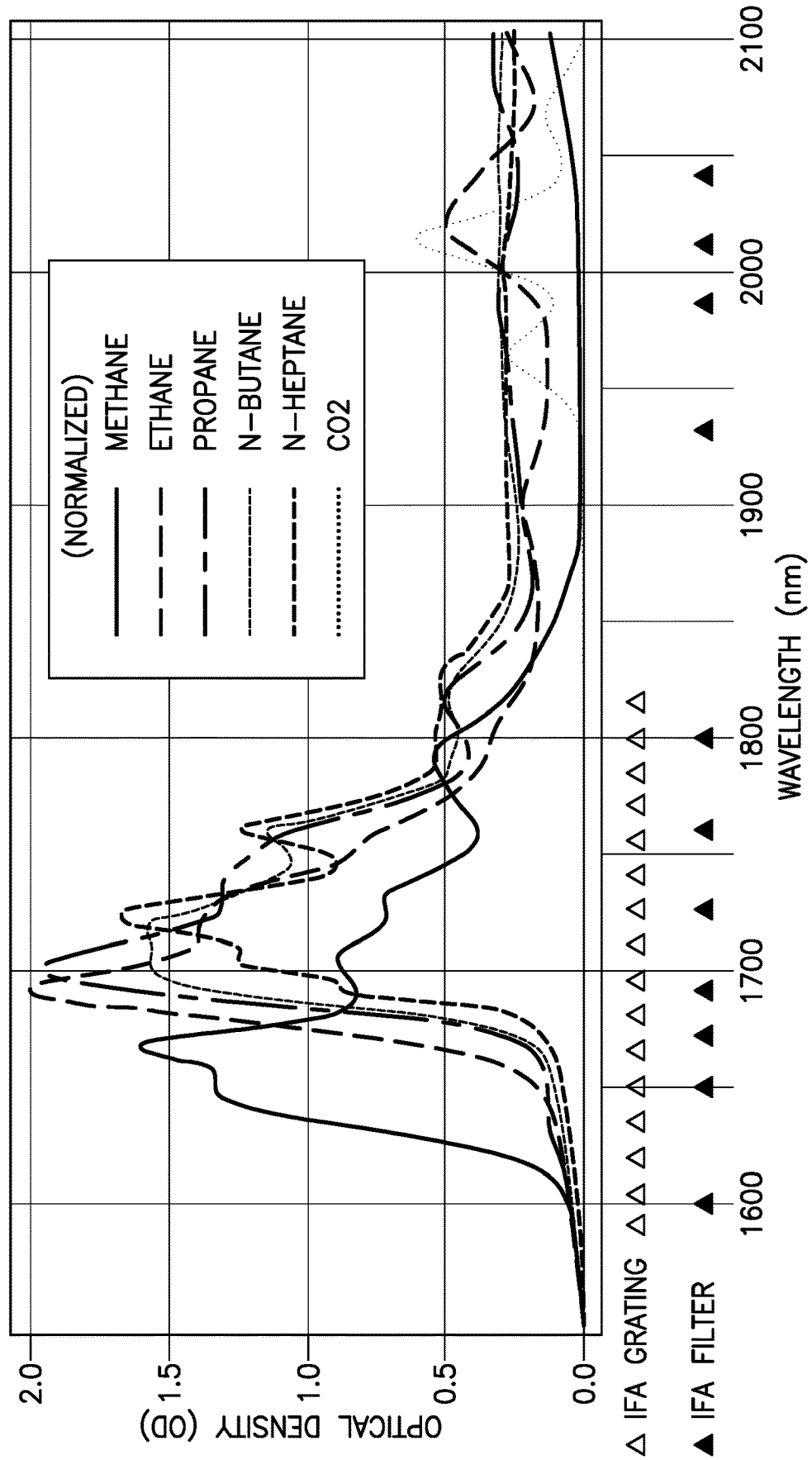
FIG. 5 is graph showing the optical spectra of a plurality of hydrocarbons and carbon dioxide at different wavelengths.

In one embodiment, instead of providing a trained learning machine that uses $T_{res}$, $C_1$, $C_{6+}$, $CO_2$ as inputs, the learning machine may be trained on optical density data from a multiplicity of wavelength channels of a DFA tool as well as other information such as formation and/or sample temperature information. As seen in FIG. 5, carbon dioxide and each specific hydrocarbon has a different optical spectrum. As is well-known, DFA tools use this fact in order to make determinations regarding the weight percentage of the different hydrocarbons (or hydrocarbon groups) present in the sample. For example, the InSitu Fluid Analyzer of Schlumberger uses a filter array spectrometer as well as a grating spectrometer. The filter array spectrometer measures wavelengths in the visible (VIS) to near-infrared (NIR) range from 400 to 2100 nm across twenty channels that indicate the color and molecular vibration absorptions of the reservoir fluid and also show the main absorption peaks of water and carbon dioxide, while the grating spectrometer has sixteen channels focused on the 1600 to 1800 nm range where reservoir fluid has characteristic absorptions that reflect molecular structure. Regardless of whether one or both of the filter array and grating spectrometer are utilized, rather than using the absorption (or transmission) information to generate weight percentages, in this embodiment, the absorption (or transmission) information may be used directly to train the learning machine. Then, once the learning machine has been trained, downhole optical (spectral) data obtained from a DFA tool such as the InSitu Fluid Analyzer of Schlumberger may be input directly into a trained model to provide a desired output such as a determination of fluid saturation pressure. It should be noted that during the learning steps of the machine learning model, the model may find that only certain channels of optical data are required to make desired determinations. In that case, when the DFA tool is run, only the data from specifically required channels would typically be input into the model.

Figure 6:
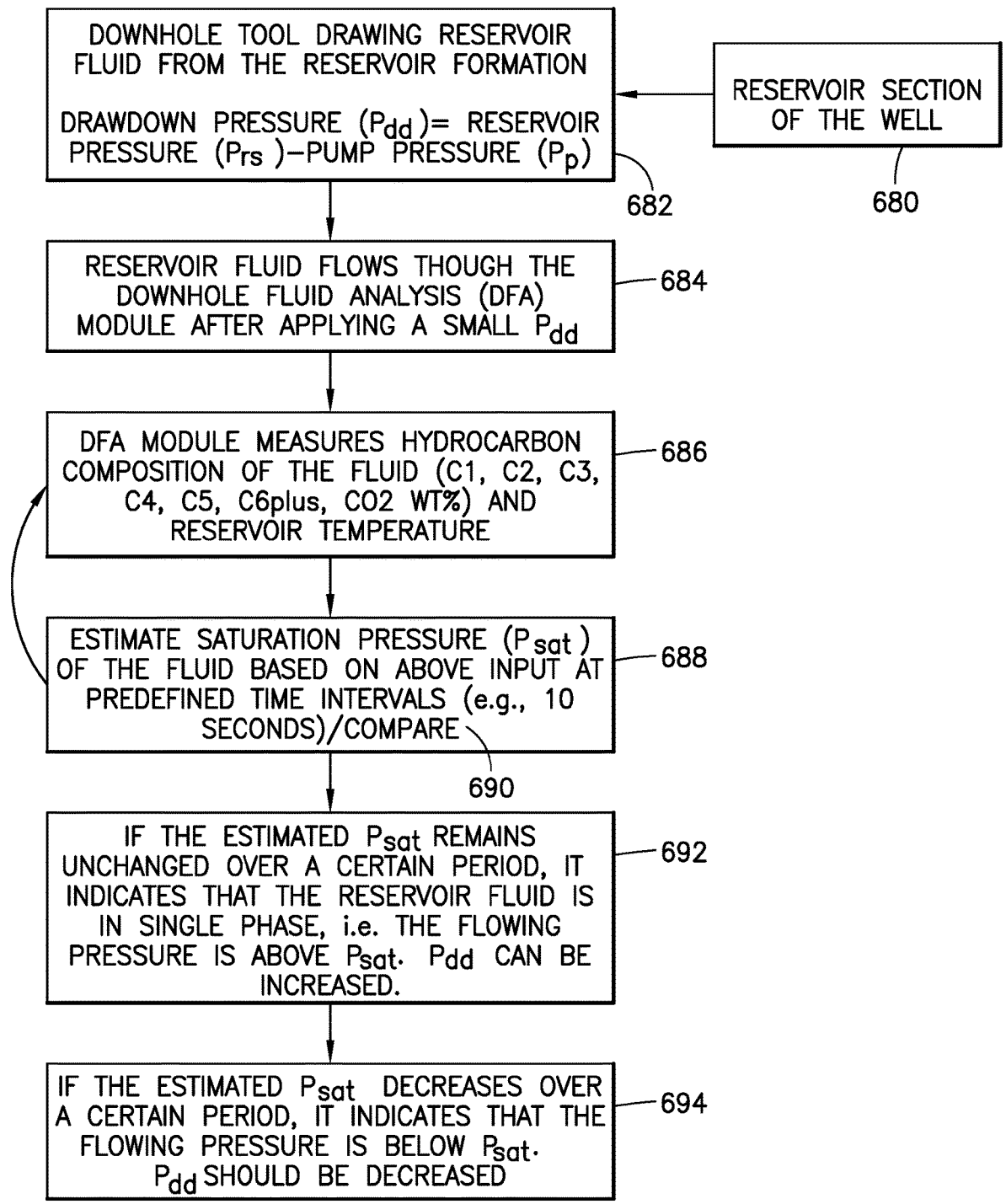
FIG. 6 is a block diagram of showing use of an in situ saturation pressure determination during downhole sampling of formation fluids.

Turning now to FIG. 6, a block diagram is provided showing one use of an in situ saturation pressure determination during downhole sampling of formation fluids. At 680, a downhole tool (such as tool 10 of FIG. 1) is located in a borehole adjacent a reservoir in the earth formation. At 682, the fluid admitting assembly of the tool is caused to engage the formation and a pump pressure $P_p$ is set so that the drawdown pressure Pad equals the reservoir pressure $P_{res}$ minus the pump pressure; i.e., $P_{dd}=P_{res}-P_p$. Typically, the initial drawdown pressure will be chosen to be small. As fluid flows at 684 through the DFA module of the tool, at 686, the module measures optical density information (absorption and/or transmission) and the system processes the information (downhole and/or uphole) in order to determine the hydrocarbon composition of the fluid as well as the carbon dioxide weight percentage. In addition, the tool measures the reservoir temperature. At 688, specific determinations of the system (e.g., $C_1$, $C_{6+}$, $CO_2$, $T_{res}$) are provided to a trained machine learning model to make a determination of $P_{sat}$. Based on the $P_{sat}$ determination, the pump pressure, and hence the drawdown pressure, may then be changed under control of a controller (18 in FIG. 1). According to one embodiment, the determination of $P_{sat}$ may be made over a predefined time interval (e.g., ten seconds). The determination made at one time may then be compared at 690 to a previous determination. If the estimated $P_{sat}$ remains unchanged as indicated at 692, the lack of change can be taken as an indication that the reservoir fluid is in a single phase; i.e., the flowing pressure is above $P_{sat}$, and the drawdown pressure can be increased in order to increase the rate at which a representative fluid sample can be collected. Conversely, if the estimated $P_{sat}$ decreases over a timeframe as indicated at 694, the change can be taken as an indication that the fluid is flowing at a pressure below the saturation pressure of the fluid, and the drawdown pressure should be decreased in order to obtain a representative fluid sample.

Some of the methods and processes described above, including processes, as listed above, can be performed by a processor. The term "processor" should not be construed to limit the embodiments disclosed herein to any particular device type or system. The processor may include a computer system. The computer system may also include a computer processor (e.g., a microprocessor, microcontroller, digital signal processor, or general-purpose computer) for executing any of the methods and processes described above.

The computer system may further include a memory such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device.

Some of the methods and processes described above can be implemented as computer program logic for use with the computer processor. The computer program logic may be embodied in various forms, including a source code form or a computer executable form. Source code may include a series of computer program instructions in a variety of programming languages (e.g., an object code, an assembly language, or a high-level language such as C, C++, or JAVA). Such computer instructions can be stored in a non-transitory computer readable medium (e.g., memory) and executed by the computer processor. The computer instructions may be distributed in any form as a removable storage medium with accompanying printed or electronic documentation (e.g., shrink wrapped software), preloaded with a computer system (e.g., on system ROM or fixed disk), or distributed from a server or electronic bulletin board over a communication system (e.g., the Internet or World Wide Web).

Alternatively or additionally, the processor may include discrete electronic components coupled to a printed circuit board, integrated circuitry (e.g., Application Specific Integrated Circuits (ASIC)), and/or programmable logic devices (e.g., a Field Programmable Gate Arrays (FPGA)). Any of the methods and processes described above can be implemented using such logic devices.

It should be appreciated that according to one aspect, "machine learning" requires a processor and cannot be conducted by human calculation without a processor.

Although only a few examples have been described in detail above, those skilled in the art will readily appreciate that many modifications are possible in the examples without materially departing from this subject disclosure. For example, while the specification has discussed making a determination of fluid saturation pressure, it will be appreciated that other determinations of fluid properties may be accomplished in situ by training a predictive model to estimate those fluid properties given a set of input parameters from a DFA tool. By way of example, determinations of properties such as the gas-oil ratio (GOR), fluid density, and formation volume factor may be made in a similar fashion. Also, a particular learning machine was described (i.e., an SVM regression model using a radial kernel), other supervised and unsupervised learning machines may be utilized. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

What is claimed is:

1. A method of determining in situ a value of a parameter of a reservoir fluid taken from a formation traversed by a borehole, comprising:
performing a first fluid analysis in real-time while a tool is concurrently in the borehole, wherein performing the first fluid analysis comprises:
drawing a first fluid into the tool, wherein the tool comprises an optical module including a spectrometer;
shining light through the first fluid in the tool and sensing with the spectrometer a first plurality of resulting signals via one or more channels of the spectrometer;
determining a first set of inputs based on the first plurality of resulting signals;
applying, via a controller, the first set of inputs to a trained statistical learning machine;
taking, via the controller, a first output of the trained statistical learning machine as a determination of the value of the parameter, wherein the trained statistical learning machine is trained utilizing a dataset of fluid properties for fluid samples as input parameters;
modifying, via the controller, the trained statistical learning machine based at least upon the first output and the first plurality of resulting signals associated with the first output; and
determining, via the controller, a subset of the one or more channels, wherein the subset of the one or more channels are associated with relevant values to determine the value of the parameter;
performing a second fluid analysis in real-time while the tool is concurrently in the borehole, wherein performing the second fluid analysis comprises:
drawing a second fluid into the tool;
shining light through the second fluid in the tool and sensing with the spectrometer a second plurality of resulting signals via the subset of the one or more channels;
determining, via the controller, a second set of inputs based on the second plurality of resulting signals;
applying, via the controller, the second set of inputs to the trained statistical learning machine;
taking, via the controller, a second output of the trained statistical learning machine as the determination of the value of the parameter; and
comparing, via the controller, the first output and the second output to determine a change in the value of the parameter; and
modifying, via the controller, a drawdown pressure of the tool based on the comparison between the first output and the second output.

2. The method according to claim 1, wherein:
the parameter is a saturation pressure of the reservoir fluid at downhole conditions.

3. The method according to claim 2, wherein:
the first set of inputs are obtained by processing the first plurality of resulting signals and the second set of inputs are obtained by processing the second plurality of resulting signals to obtain weight fractions of at least C1, C6+, CO2, wherein each of the first and second sets of inputs includes weight fractions and a reservoir temperature.

4. The method according to claim 1, wherein:
the trained statistical learning machine is a support vector machine using a regression model.

5. The method according to claim 3, wherein:
modifying the drawdown pressure of the tool comprises modifying a first drawdown pressure to a second drawdown pressure different than the first drawdown pressure based on the relative values obtained for the saturation pressure of the first fluid and the second fluid.

6. The method according to claim 5, wherein:
modifying comprises increasing the drawdown pressure such that the second drawdown pressure is greater than the first drawdown pressure when the saturation pressure of the first fluid and the second fluid is the same.

7. The method according to claim 5, wherein:
modifying comprises decreasing the drawdown pressure such that the second drawdown pressure is less than the first drawdown pressure when the saturation pressure of the first fluid and the second fluid has changed.

8. The method according to claim 2, wherein:
the first plurality of resulting signals are optical density indications of the one or more channels of the spectrometer and the second plurality of resulting signals are optical density indications of the subset of the one or more channels.

9. The method of claim 8, wherein:
the trained statistical learning machine is a support vector machine using a regression model.

10. A method, comprising:
obtaining samples of reservoir fluid from one or more formations at measured formation temperatures;
analyzing the saturation pressures of the samples in a laboratory;
analyzing the samples for optical density as a function of wave-length to obtain indicative information of the different makeups of the samples;
using the measured formation temperatures, saturation pressures and indicative information as at least training data to train a statistical learning machine, wherein the measured formation temperatures, saturation pressures and indicative information comprises a dataset of fluid properties for training the statistical learning machine and wherein the dataset is split into a training portion for training the statistical learning machine and a testing portion for testing the statistical learning machine;
performing a first fluid analysis in real-time while a tool is concurrently in a borehole, wherein the first fluid analysis comprises:
 drawing a first fluid into the tool at a first drawdown pressure, wherein the tool comprises an optical module including a spectrometer, and the first fluid is taken from a downhole formation at a measured downhole formation temperature;
 shining light through the first fluid in the tool and sensing with the spectrometer a plurality of resulting signals via one or more channels of the spectrometer;
 applying indications of the resulting signals and the measured downhole formation temperature as inputs to the trained statistical learning machine, wherein the indications of the resulting signals are optical density indications of a plurality of channels of the spectrometer, wherein the optical density indications are the inputs to the trained statistical learning machine;
 taking an output of the trained statistical learning machine as a determination of a saturation pressure of the first fluid;
 modifying the trained statistical learning machine based at least upon the output and the resulting signals associated with the first fluid; and
 determining a subset of the one or more channels of the spectrometer, wherein the subset of the one or more channels are associated with relevant values to determine the saturation pressure;
performing a second fluid analysis in real-time while the tool is concurrently in the borehole, wherein the second fluid analysis comprises:
 drawing a second fluid into the tool;
 shining light through the second fluid in the tool and sensing with the subset of the one or more channels of the spectrometer a plurality of resulting signals related to the second fluid;
 applying indications of the resulting signals related to the second fluid as inputs to the trained statistical learning machine; and
 taking an output of the trained statistical learning machine as a determination of a saturation pressure of the second fluid; and
modifying the first drawdown pressure to a second drawdown pressure different than the first drawdown pressure based on the relative values obtained for the saturation pressure of the first fluid and the second fluid.

11. The method of claim 10, wherein:
the statistical learning machine is a support vector machine using a regression model.

12. The method of claim 10, wherein:
the indications of the resulting signals are obtained by processing the resulting signals to obtain weight fractions of at least C1, C6+, CO2, wherein the weight fractions are the inputs to the trained statistical learning machine.

13. The method according to claim 10, wherein:
modifying comprises increasing drawdown pressure such that the second drawdown pressure is greater than the first drawdown pressure when the saturation pressure of the first fluid and the second fluid is the same.

14. The method according to claim 10, wherein:
modifying comprises decreasing drawdown pressure such that the second drawdown pressure is less than the first drawdown pressure when the saturation pressure of the first fluid and the second fluid has changed.

15. The method according to claim 1, comprising determining a training set and a testing set, wherein the training set and testing set are comprised of randomly selected data from the first output and the corresponding first set of inputs, the second output and the corresponding second set of inputs, or both.

16. The method according to claim 15, comprising training the statistical learning machine with the training set, wherein the training set further includes laboratory data.

17. The method according to claim 15, comprising performing a consistency check for the training set and the testing set to remove outliers.

* * * * *